US008935098B2

(12) United States Patent
Di Carlo et al.

(10) Patent No.: US 8,935,098 B2
(45) Date of Patent: Jan. 13, 2015

(54) METHOD AND DEVICE FOR HIGH THROUGHPUT CELL DEFORMABILITY MEASUREMENTS

(75) Inventors: Dino Di Carlo, Los Angeles, CA (US); Daniel R. Gossett, Los Angeles, CA (US); Henry T. K. Tse, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/823,109

(22) PCT Filed: Sep. 16, 2011

(86) PCT No.: PCT/US2011/052041
§ 371 (c)(1),
(2), (4) Date: Mar. 14, 2013

(87) PCT Pub. No.: WO2012/040067
PCT Pub. Date: Mar. 29, 2012

(65) Prior Publication Data
US 2013/0177935 A1     Jul. 11, 2013

Related U.S. Application Data

(60) Provisional application No. 61/385,268, filed on Sep. 22, 2010.

(51) Int. Cl.
*G01N 33/483* (2006.01)
*C12M 1/34* (2006.01)
(Continued)

(52) U.S. Cl.
CPC .............. *C12Q 1/02* (2013.01); *G01N 15/1459* (2013.01); *G06F 19/10* (2013.01); *G01N 33/574* (2013.01); *G01N 2015/1495* (2013.01); *G01N 15/1484* (2013.01)
USPC .......................... 702/21; 435/40.5; 435/40.51

(58) Field of Classification Search
None
See application file for complete search history.

(56) References Cited

FOREIGN PATENT DOCUMENTS

| KR | 10-0889617 | 3/2009 |
|----|------------|--------|
| KR | 10-0889618 | 3/2009 |

(Continued)

OTHER PUBLICATIONS

Shelby, "A microfluidic model for single-cell capillary obstruction by *Plasmodium falciparum* infected erythrocytes," PNAS, vol. 100, pp. 14618-14622, 2003.*

(Continued)

*Primary Examiner* — Lori A. Clow
*Assistant Examiner* — G. Steven Vanni
(74) *Attorney, Agent, or Firm* — Vista IP Law Group LLP

(57) ABSTRACT

A system is disclosed that enables the automated measurement of cellular mechanical parameters at high throughputs. The microfluidic device uses intersecting flows to create an extensional flow region where the cells undergo controlled stretching. Cells are focused into streamlines prior to entering the extensional flow region. In the extensional region, each cell's deformation is measured with an imaging device. Automated image analysis extracts a range of independent biomechanical parameters from the images. These may include cell size, deformability, and circularity. The single cell data that is obtained may then be used to in a variety of ways. Scatter density plots of deformability and circularity may be developed and displayed for the user. Mechanical parameters such as deformability and circularity may be gated or thresholded to identify certain cells of interest or sub-populations of interest. Similarly, the mechanical data obtained using the device may be used as cell signatures.

23 Claims, 13 Drawing Sheets

(51) Int. Cl.
G01N 1/30 (2006.01)
G01N 15/14 (2006.01)
G06F 19/10 (2011.01)
G01N 33/574 (2006.01)
C12Q 1/02 (2006.01)

(56) References Cited

FOREIGN PATENT DOCUMENTS

| KR | 10-0965222 | 6/2010 |
|---|---|---|
| WO | WO 2004/113908 A1 | 12/2004 |
| WO | WO 2009/069418 A1 | 6/2009 |

OTHER PUBLICATIONS

Dylla-Spears, "Single-molecule sequence detection via microfluidic planar extensional flow at a stagnation point," Lab on a Chip, vol. 10, pp. 1543-1549, Mar. 2010.*
Yap, "Cytoskeletal remodeling and cellular activation during deformation of neutrophils into narrow channels," vol. 99, pp. 2323-2330, 2005.*
Lincoln, "Deformability-Based Flow Cytometry," Cytometry Part A, vol. 59A, pp. 203-209, 2004.*
Dobbe, "Measurement of the Distribution of Red Blood Cell Deformability Using an Automated Rheoscope," Cytometry (Clinical Cytometry), vol. 50, pp. 313-325, 2002.*
Squires, "Microfluidics: Fluid physics at the nanoliter scale," Rev. of Modern Physics, vol. 77, pp. 977-1026, 2005.*
Zheng, "Formation of Droplets of Alternating Composition in Microfluidic Channels and Applications to Indexing of Concentrations in Droplet-Based Assays," Anal. Chem., vol. 76, pp. 4977-4982, 2004.*
Young, "High-Throughput Microfluidic Mixing and Multiparametric Cell Sorting for Bioactive Compound Screening," J Biomol Screen, vol. 9, pp. 103-111, 2004.*
Gossett, D.R. et al., Deformability Cytometry: High-Throughput, Continuous Measurement of Cell Mechanical Properties in Extensional Flow, 14th International Conference on Miniaturized System for Chemistry and Life Sciences Oct. 3-7, 2010, Groningen, The Netherlands (3pages).
PCT Written Opinion of the International Search Report for PCT/US2011/052041, Applicant: The Regents of the University of California, Form PCT/ISA/237, dated Apr. 10, 2012 (5pages).
PCT International Preliminary Report on Patentability (Chapter I of the Patent Cooperation Treaty) for PCT/US2011/052041, Applicant: The Regents of the University of California, Form PCT/IB/326 and 373, dated Apr. 4, 2013 (7pages).

Bhagat, Ali Asgar et al., Intertial microfluidics for sheath-less high-throughput cytometry, Biomed. Microdevices 12 (2), 187-195 (2010).
Choi, Sungyoung et al., Sheathless hydrophoretic particle focusing in a microchannel with exponentially increasing obstacle arrays, Anal Chem., 80(8):3035-9 (2008).
Cross, Sarah E. et al., Nanomechanical analysis of cells from cancer patients. Nat Nano 2:780-783 (2007).
Di Carlo, Dino et al., Dynamic Single-Cell Analysis for Quantitative Biology, Analytical Chemistry 78:7918-7925 (2006).
Di Carlo, Dino, Inertial microfluidics. Lab Chip 9:3038-3046 (2009).
Di Carlo, Dino et al., Continuous inertial focusing, ordering, and separation of particles in microchannels. Proc Natl Acad Sci USA 104:18892-18897 (2007).
Di Carlo, Dino et al., Particle Segregation and Dynamics in Confined Flows, Phys. Rev. Lett. 102 (2009).
Gossett, Daniel R. et al., Particle focusing mechanisms in curving confined flows, Anal Chem 81:8459-8465 (2009).
Guck, Jochen et al., Optical Deformability as an Inherent Cell Marker for Testing Malignant Transformation and Metastatic Competence. Biophysical Journal 88:3689-3698 (2005).
Lee, Wonhee et al., Dynamic self-assembly and control of microfluidic particle crystals, Proc. Natl. Acad. Sci. U.S.A 107, 22413-22418 (2010).
Mao, Xiaole et al., single-layer planar on-chip flow cytometer using microfluidic drifting based three-dimensional (3D) hydrodynamic focusing, Lab Chip, 9, 1583-1589 (2009).
Oakey, John et al., Particle Focusing in Staged Inertial Microfluidic Devices for Flow Cytometry, Anal. Chem., 82, 3862-3867 (2010).
Park, Jae-Sung et al., Continuous focusing of microparticles using intertial lift force and vorticity via multi-orifice microfluidic channels, Lab on a Chip, 9, 939-48 (2009).
Perkins, Thomas T. et al., Single Polymer Dynamics in an Elongational Flow, Science 276:2016-2021 (1997).
Sraj, Ihab et al., Cell deformation cytometry using diode-bar optical stretchers, J Biomed Opt 15 (2010).
Suresh, S. et al., Connections between single-cell biomechanics and human disease states: gastrointestinal cancer and malaria. Acta Biomater 1:15-30 (2005).
Thery, Manuel et al., Get round and stiff for mitosis. HFSP J 2:65-71 (2008).
Yamada, Masumi et al., Hydrodynamic filtration for on-chip particle concentration and classification utilizing microfluidics Lab Chip, 5, 1233-1239 (2005).
PCT International Search Report for PCT/US2011/052041, Applicant: The Regents of the University of California, Form PCT/ISA/210 and 220, dated Apr. 10, 2012 (7pages).

* cited by examiner

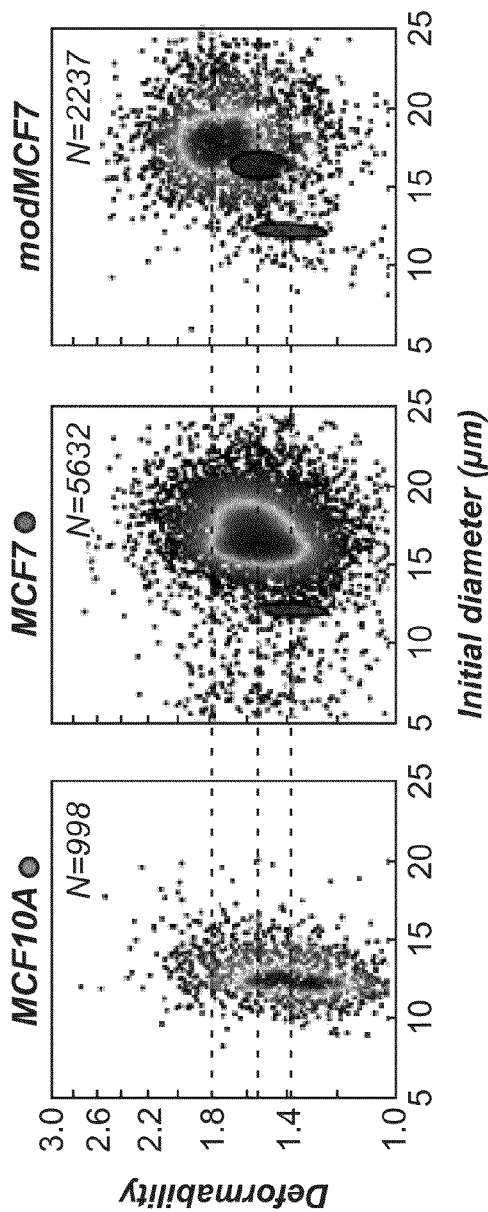
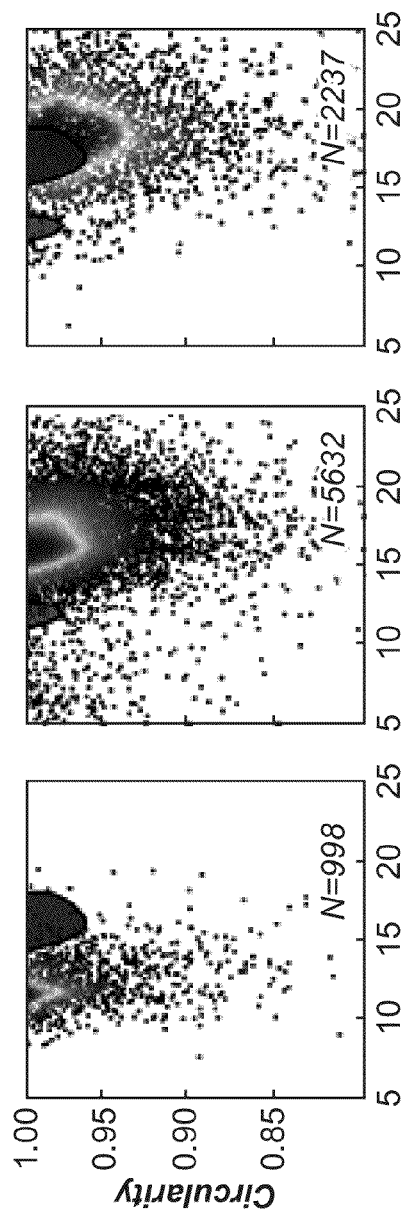
FIG. 9A
FIG. 9B

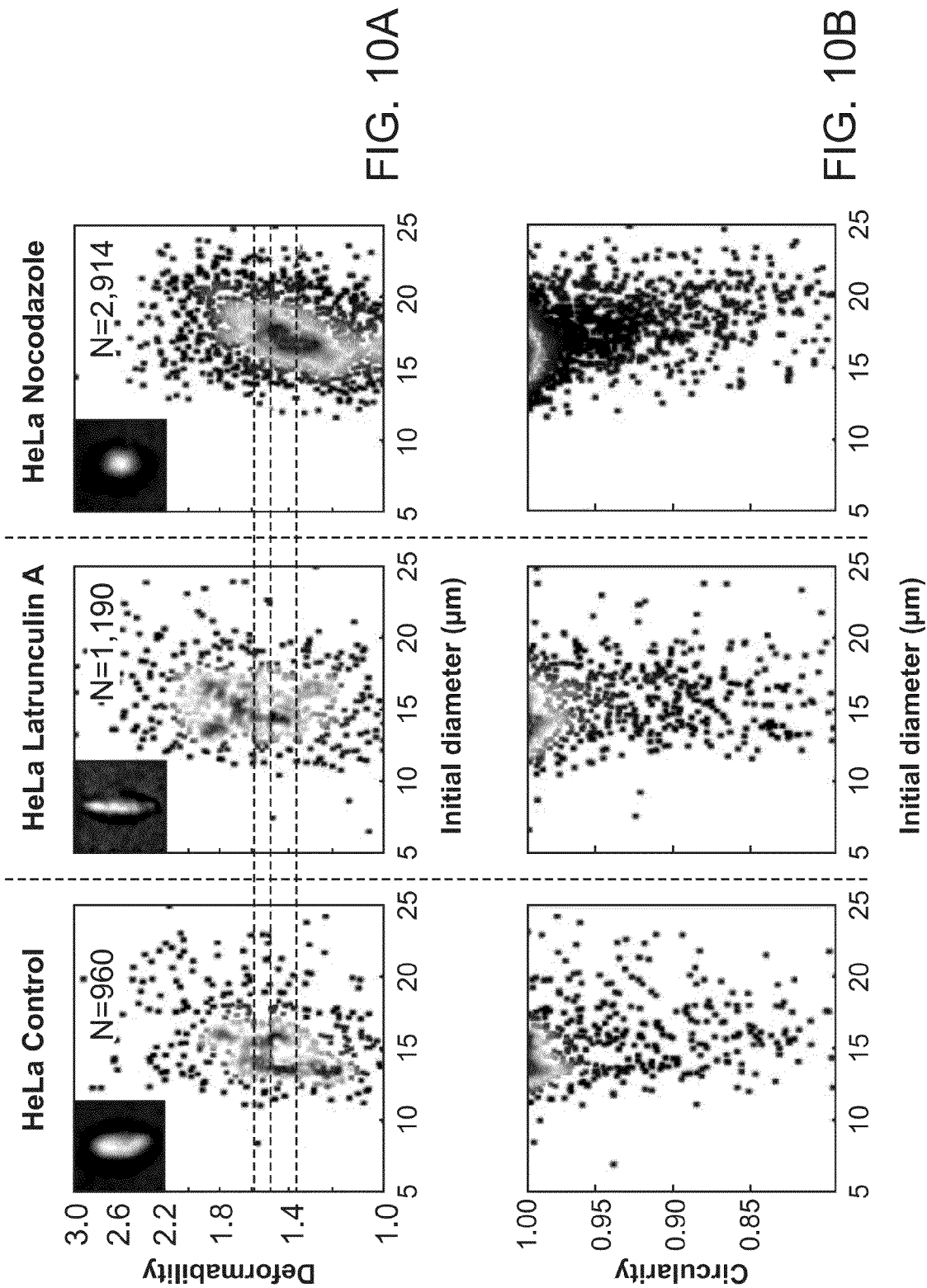

Standard Negative Profile
N=9
LHD=0.9%

Standard Adenocarcinoma Profile
N=10
LHD=21.3%

ND DEVICE FOR HIGH
METHOD AND DEVICE FOR HIGH THROUGHPUT CELL DEFORMABILITY MEASUREMENTS

RELATED APPLICATION

This Application is a U.S. National Stage filing under 35 U.S.C. §371 of International Application No. PCT/US2011/052041, filed Sep. 16, 2011, which claims priority to U.S Provisional Patent Application No. 61/385,268 filed Sep. 22, 2010. The contents of the aforementioned applications are hereby incorporated herein by reference in their entirely. Priority to the aforementioned applications are hereby expressly claimed in accordance with 35 U.S.C. §§119, 120, 365 and 371 and any other applicable statutes.

STATEMENT REGARDING FEDERALLY SPONSORED RESEARCH AND DEVELOPMENT

This invention was made with Government support under Grant No. W81XWH-10-1-0519, awarded by the U.S. Army, Medical Research and Materiel Command and Grant No. 0930501, awarded by the National Science Foundation. The Government has certain rights in the invention.

FIELD OF THE INVENTION

The field of the invention generally relates to microfluidic devices and methods for measuring the size, circularity, and deformability of cells. The field of the invention also pertains to devices and methods for utilizing these measured parameters as biomarkers and cell phenotype identification purposes.

BACKGROUND

There is growing evidence that cell deformability (i.e., the degree to which a cell changes shape under an applied load) is a useful indicator of abnormal cytoskeletal changes and may provide a label-free biomarker for determining cell states or properties such as metastatic potential, cell cycle stage, degree of differentiation, and leukocyte activation. Clinically, a measure of metastatic potential could guide treatment decisions, or a measure of degree of differentiation could prevent transplantation of undifferentiated, tumorigenic stem cells in regenerative therapies. For drug discovery and personalized medicine, a simple measure of cytoskeletal integrity could allow screening for cytoskeletal-acting drugs or evaluation of cytoskeletal drug resistance in biopsied samples. Currently, these applications often require costly dyes, antibodies, and other reagents, along with skilled technicians to prepare samples. A simple label-free deformability measurement in which cells are minimally handled has the potential to greatly reduce costs and allow routine cell screening and classification in clinical and research applications.

Current platforms and techniques that measure cell deformability have suffered from a number of limitations. These include low throughput as well as inconsistent results. As a result, these technologies have not had any significant clinical impact. A wide variety of platforms have been engineered to perform mechanical measurements on cells. Generally, these techniques can be divided into two categories based on the samples they act on: bulk and single-cell. Bulk platforms, such as microfiltration, tend to have high throughput, but they yield one endpoint measurement and do not take into account heterogeneity within the sample population of cells. Disease may develop from abnormalities in a single cell thus accurately detecting rare events or local variations is important and bulk measurement of these types of samples may result in misleading averages. Single-cell platforms that can assay this heterogeneity include micropipette aspiration, atomic force microscopy (AFM), magnetic bead-based rheology, microfluidic optical stretching, and biophysical flow cytometry.

However, these approaches are typically optimized for biophysics research and operate at low rates at around 1 cell/minute for AFM and optical stretching. Applications in clinical diagnostics or drug screening will necessarily require large sample sizes to obtain statistically significant results. This cannot reasonably be achieved using low throughputs on the order of 1 cell/minute. Further, these techniques also suffer from other disadvantages. AFM, for example, requires a skilled operator and measurements are slow. Rheological techniques can yield drastically different mechanical properties that are difficult to standardize even amongst a single cell type. In addition, these techniques require microscopic observation at high magnification for a period of time such that the overall throughput is very low (<<1 cell/minute). The manual, low-throughput nature of current methods that measure cell mechanical properties has limited the capability for development of practical biomechanical biomarkers for translational use, as well as limited the progress of understanding molecular components underlying cell mechanical properties.

SUMMARY

In one embodiment, a microfluidic device is disclosed that enables the automated measurement of cellular mechanical parameters at high throughputs greater than 1,000 cells/second. The microfluidic device uses intersecting flows to create an extensional flow region where the cells undergo controlled stretching. Cells are focused into streamlines (e.g., a continuous stream of single cells in a streamline) prior to entering the extensional flow region. In the extensional region, each cell's deformation is measured with an imaging device. Automated image analysis extracts a range of independent biomechanical parameters from the images. These may include cell size, deformability, and circularity. The single cell data that is obtained may then be used in a variety of ways. For example, scatter density plots of deformability and circularity may be developed and displayed for the user similar to the way in which traditional flow cytometry scatter plots are used. Mechanical parameters such as deformability and circularity may be gated or thresholded to identify certain cells of interest or sub-populations of interest. Similarly, the mechanical data obtained using the device may be used as cell signatures.

Generally, the method for high throughput cell deformability measurements involves positioning the cells along a focused path or streamline at relatively high flow rates. The cells are then delivered to an extensional region wherein each cell is subject to uniformly controlled deformation (e.g., cell stretching). The imaging device captures this controlled deformation whereby the images are subject to morphological analysis to determine cell size, cell deformability, and cell circularity. This data can then be quickly presented to the user in a useful format (e.g., scatter plot) or further processed to present the user with useful information regarding the tested cells. For example, the method may be used to screen a sample of cells for a diseased state (e.g., cancer), identify useful information regarding stem cell differentiation, or be further subject to additional data mining for predictive information. The method may also complement existing cellular analysis tools to provide more confidence in decision making.

The method is also beneficial in that it reduces costs because of the reduced reagent consumption. Similarly, there is a reduction in labor costs because the automatic method eliminates time consuming steps such as pipetting, centrifugation, etc.

In one embodiment of the invention, a system for measuring particle (e.g., cell) deformability includes a substrate containing first and second microfluidic channels dimensioned to carry cells therein and an extensional region comprising an intersection of the first and second microfluidic channels, wherein the first and second microfluidic channels intersect in substantially opposite directions. The system includes at least one outlet channel coupled to the extensional region and an imaging device configured to capture a plurality of image frames of cells passing through the extensional region and at least one processor configured to calculate a morphological parameter of the cell. These parameters may include cell size, cell deformability, and cell circularity of cells passing through the extensional region. Additional parameters include cell shape, cell granularity, and intracellular structure.

In another embodiment of the invention, a method of measuring particle (e.g., cell) deformability includes focusing a plurality of cells in first and/or second microfluidic channels dimensioned to carry cells therein. For example, in one configuration, cells are carried in opposing microfluidic channels that intersect as described below. In another configuration, cells are only carried by one of the two intersecting microfluidic channels. The cells of the first and/or second microfluidic channels are then intersected in an extensional region configured to apply stress to cells passing therein. A plurality of image frames of the cells are obtained, wherein the plurality of image frames contain images of cells prior to entering the extensional region and during exposure to the extensional region. One or more dimensional parameters of the cells are measured from the plurality of image frames prior to entering the extensional region and during exposure to the extensional region. The deformability of a cell is determined based at least in part on the change of the one or more dimensional parameters occurring during exposure to the extensional region.

In another embodiment, a system for measuring particle deformability includes a substrate containing first and second microfluidic channels dimensioned to carry cells therein. The system includes an extensional region comprising an intersection of the first and second microfluidic channels, wherein the first and second microfluidic channels intersect in substantially opposite directions. At least one outlet channel is coupled to the extensional region. The system further includes an optical collector configured to capture diffracted or refracted light from cells passing through the extensional region and at least one processor configured to calculate a morphological parameter of the particle passing through the extensional region.

In another embodiment, a system for measuring particle deformability includes a substrate containing a microfluidic channel dimensioned to carry cells therein and an extensional region comprising a junction wherein the velocity of the flow in the incoming flow direction abruptly decreases to substantially zero. At least one outlet channel is coupled to the junction of the extensional region. The system includes an imaging device configured to capture a plurality of image frames of cells passing through the extensional region and at least one processor configured to calculate a morphological parameter of the particle passing through the extensional region.

BRIEF DESCRIPTION OF THE DRAWINGS

FIG. 9A illustrates scatter plots of cell deformability as function of initial diameter for normal cells (MCF10A), cancerous cells (MCF7), and the same cancerous cell line modified to have increased motility or metastatic potential (modMCF7).

FIG. 9B illustrates scatter plots of cell circularity as function of initial diameter for normal cells (MCF10A), cancerous cells (MCF7), and the same cancerous cell line modified to have increased motility or metastatic potential (modMCF7).

FIG. 10A illustrates scatter plots of cell deformability as function of initial diameter for HeLa cells (control), HeLa cells treated with Latrunculin A, and HeLa cells treated with Nocodazole.

FIG. 10B illustrates scatter plots of cell circularity as function of initial diameter for HeLa cells (control), HeLa cells treated with Latrunculin A, and HeLa cells treated with Nocodazole.

DETAILED DESCRIPTION OF THE ILLUSTRATED EMBODIMENTS

Figure 1:
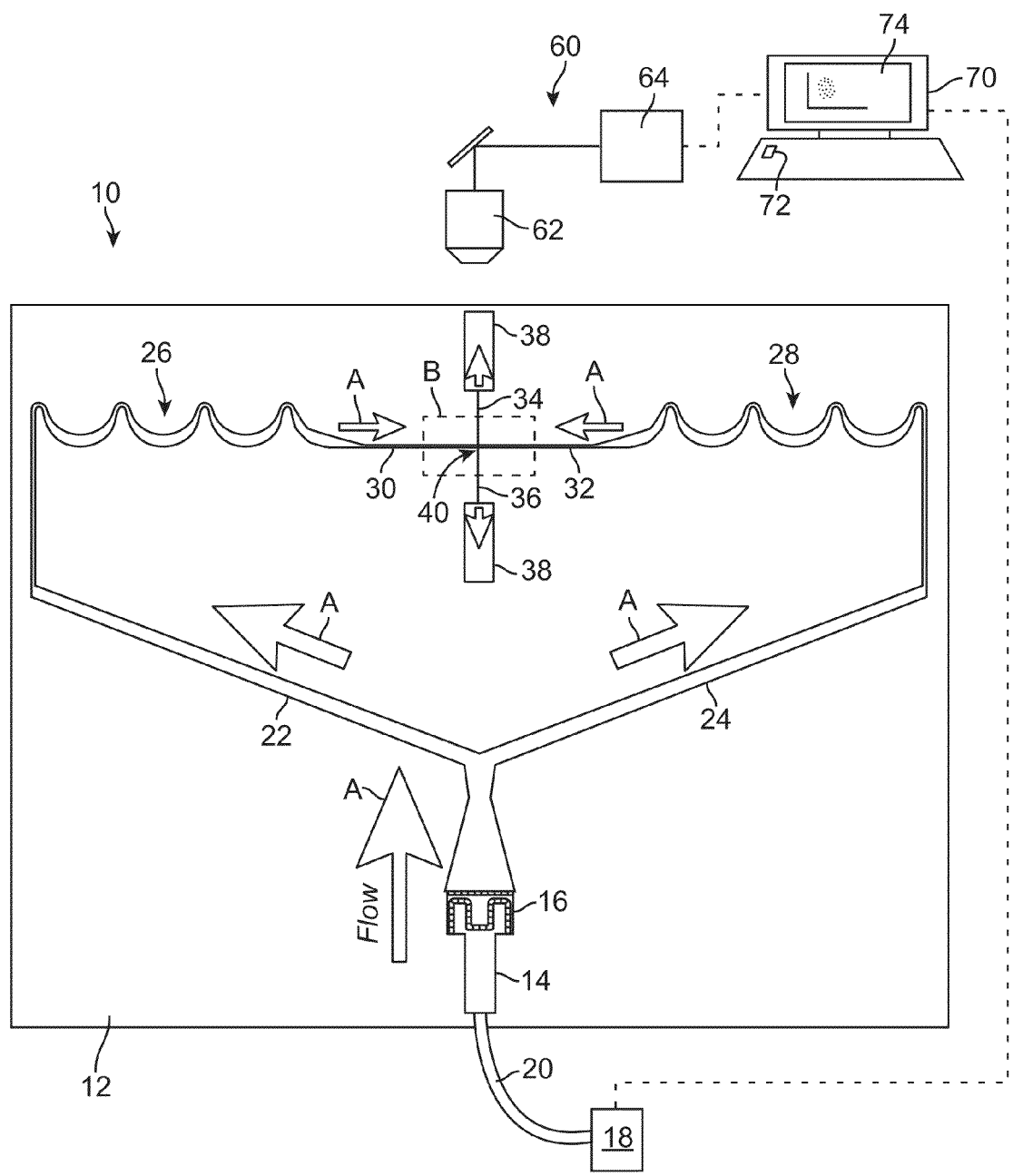
FIG. 1 illustrates a schematic view of a system for measuring cell deformability according to one embodiment.

FIG. 1 illustrates a system 10 for measuring particle deformability according to one embodiment. Particles may include cells as well as other structures such as hydrogel particles, oil droplets, and the like. The system 10 has particular applicability for measuring deformability of cells but the system may also be used for measuring deformation of other small particles. The system 10 is preferably implemented in microfluidic format on a substrate 12. The substrate 12 may include any number of structures commonly used for microfluidic applications including glass, polymers, or composite structures. For example, the microfluidic features such as the inlets, outlets, extensional regions, channels, focusing regions, and the like may be formed in PDMS which is then bonded to another substrate like glass. The microfluidic features illustrated in FIG. 1 may be designed using conventional software (e.g., AutoCAD software available from Autodesk, San Rafael, Calif.). Transparency photomasks for the designs can be printed at 20,000 dots per inch (CAD/Art Services, Inc., Bandon, Oreg., USA). Molds for replica molding using these masks are prepared using negative photoresist, such as SU-8 50 (MicroChem, Newton, Mass.). The negative photoresist is spun on a 4 inch Silicon wafer at 4000 rotations per minute. The coated wafer is then soft baked at 65° C. for 5 minutes then 95° C. for 15 minutes. The wafer was then exposed under near UV radiation at 8.0 mW/cm2 for 30 seconds. A post-exposure bake of the wafer is carried out at 65° C. for 2 minutes then at 95° C. for 3.5 minutes. The unexposed photoresist is developed in SU-8 Developer (MicroChem) until an isopropyl alcohol rinse produced no white film. The height of the microfluidic features may vary but is generally on the order of several or more microns (e.g., about 28 µm). Of course, the height used in a particular system 10 may vary.

The mold that is created can be taped to the lower plate of a Petri dish with features facing up and an approximately 6 mm layer of Sylgard 184 Silicone Elastomer (Dow Corning, Midland, Mich., USA), polydimethylsiloxane (PDMS), mixed 10 parts base to 1 part curing agent, is poured on top. The cast mold was placed in a vacuum chamber and the chamber was evacuated for 30 minutes to remove air from the curing polymer. It was then moved to an oven set to 65° C. for 3 hours. The devices were cut from the mold and inlet and outlets were punched into the cured PDMS polymer. The devices were then placed in a plasma cleaner along with slide glasses to be activated. After a 30 second exposure to air plasma the activated surfaces of PDMS and glass were placed in contact to form permanent covalent bonds between the two materials.

Still referring to FIG. 1, the system includes an inlet 14 through which a fluid laden with cells is flowed. Located in or adjacent to the inlet 14 is an optional filter 16 that may be used to filter out dust or aggregate particulate matter. The filter 16 may include, for instance, posts or others physical impediments to flow of particulate matter above a certain size. Of course, cells and other particles of interest can flow past the filter 16. A pump 18 is connected to the inlet 14 via a conduit 20 or the like. The pump 18 may include a syringe pump (e.g., PHD 2000 syringe pump, Harvard Apparatus, Holliston, Mass.), pressure pump, or other pumping device known to those skilled in the art. The pump 18 pumps a solution containing cells into the inlet 14 at a uniform flow rate. The actual rate of flow may be adjusted or tuned by the pump 19 to achieve desired mechanical deformations of the cells. For instance, low flow rates may result in non-uniform mechanical stretching while high flow rates may result in cells that are stretched beyond the imaging window (described in more detail below) which results in saturation of the measurements. The optimal flow rate is one where the cells reach the center of the extensional flow (e.g., intersecting flows) where they deform in a non-saturating amount. Flow rates vary depending on the size of the microfluidic features formed in the system 10. For instance, channels having a diameter of 67 µm had an optimized flow rate of 1075 µL/minute while a smaller diameter channel (44 µm) had an optimized flow rate of 600 µL/minute. Cells are suspended in a carrier fluid that is run through the system 10. The density of cells may vary but generally falls within the range of about 200,000 cells/mL and about 500,000 cells/mL.

Downstream of the inlet 14 the system 10 includes two branch channels 22, 24 operatively coupled to the common inlet 14. Flow thus occurs in the direction of arrows A of FIG. 1. The branch channels 22, 24 both lead to respective focusing regions 26, 28. The focusing regions serve to align the cells to the same streamlines prior to entering the extensional region 40 whereby cells undergo deformation. This ensures that each cell, traveling at the same downstream velocity, experiences the same force field upon entering the extensional region 40. A variety of different focusing techniques can be used including hydrodynamic focusing, sheath focusing, dielectrophoretic focusing, ultrasonic focusing and inertial focusing. Inertial focusing has the advantage that pinching sheath flows are not needed to steer cells to a precise position, an improvement that leads to a single input robust technology. Inertial focusing curving, confined flows is illustrated in FIG. 1. Details regarding this type of inertial focusing may be seen in, for example, D. R. Gossett et al., "Particle focusing mechanisms in curving confined flows," Analytical Chemistry, 81, 8459 (2009), which is incorporated by reference herein.

Still referring to FIG. 1, the cells leave the respective focusing regions 26, 28 with the cells aligned along streamlines contained in first and second microfluidic channels 30, 32. The cells proceed along the first and second microfluidic channels 30, 32 whereby the extensional region 40 is reached. The extensional region 40 includes an intersection of the first and second microfluidic channels 30, 32 in substantially in opposite directions. That is to say, the first and second microfluidic channels 30, 32 are substantially coaxially aligned with respect to one another. Namely, the flow and cells contained therein are directed head-on at one another in a crossing channel forming a + pattern to create a region of large deceleration whereby the cells undergo mechanical stress thereby causing, depending on the nature of the cell, deformation. The system 10 of FIG. 1 further includes two microfluidic outlet channels 34, 36 that are oriented substantially perpendicular with respect to first and second microfluidic channels 30, 32. The microfluidic outlet channels 34, 36 terminate at outlets 38. The outlets 38 may be coupled to tubing (not shown) with free ends directed to a waste receptacle or the like.

Figure 2:
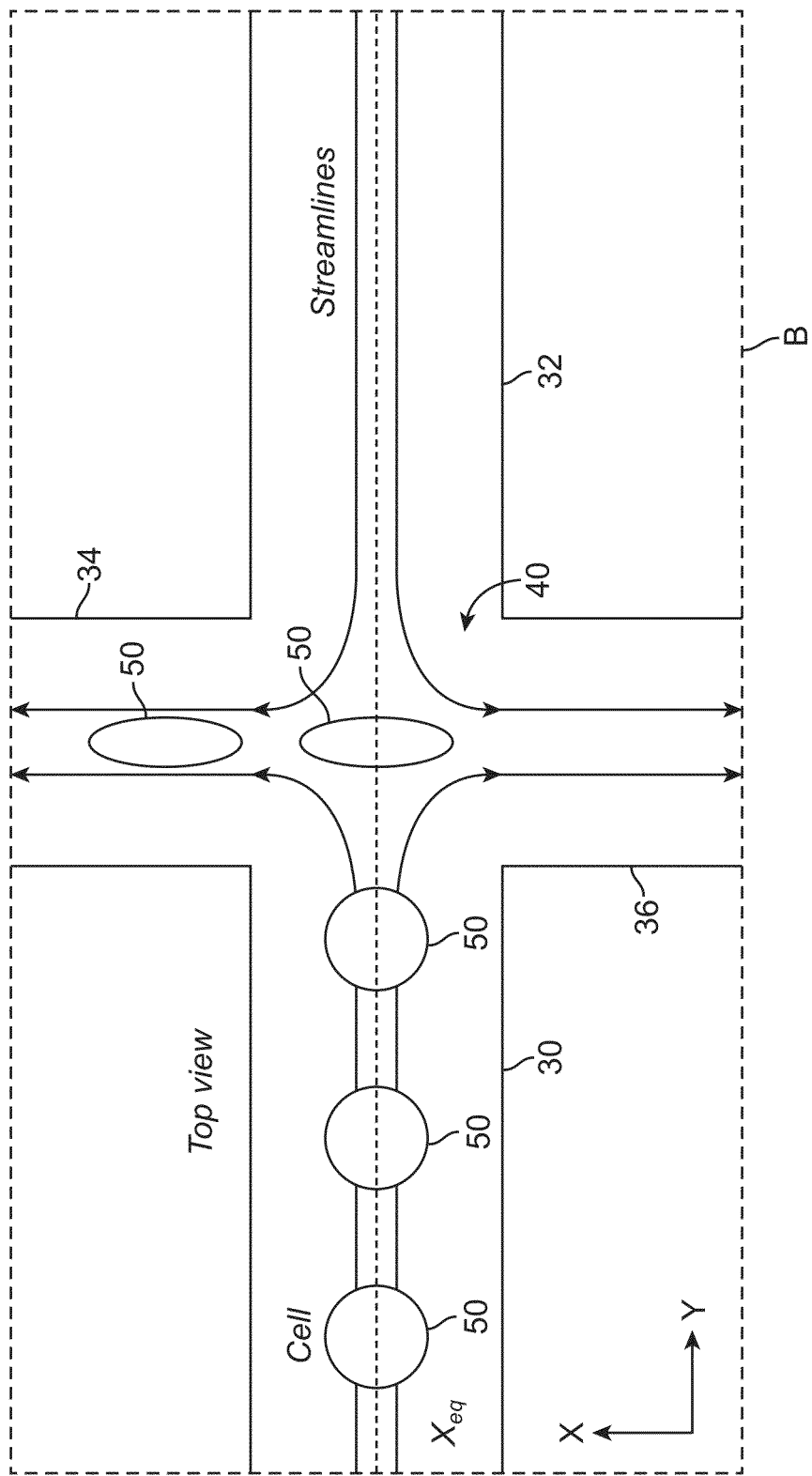
FIG. 2 is a magnified view of region B of FIG. 1 illustrating cells entering the extensional region.

FIG. 2 is enlarged view of region B of FIG. 1 illustrating the first and second microfluidic channels 30, 32 as well as the first and second microfluidic outlet channels 34, 36 intersecting in the extensional region 40. As explained below, region B may coincide substantially with the field of view (FOV) of the imaging system. Cells 50 are illustrated aligned along a lateral equilibrium streamline ($X_{eq}$) prior to entering the extensional region 40. The extensional region 40 contains purely stretching flow. As the cells 50 sequentially enter the extensional region 40, they are subject to the stretching flow within the extensional region 40 and undergo deformation. As explained below, this deformation is then imaged whereby one or more dimensional parameters are extracted. These dimensional parameters are then used to determine cell size, cell deformability, and cell circularity, or other morphological parameters such as cell shape, cell granularity, and intracellular structure. Cell shape is generally a function that defines the edge of the object. The shape could be spherical, ellipsoid, star shaped, etc. Granularity refers to the spatial frequency of variation in the optical contrast/index of refraction within a cell. Intercellular structure refers to the size and shape of objects internal to the cell that have optical contrast. This may include cellular organelles such as the cell nucleus or the like. Moreover, it may be desirable to measure one or more morphological parameters prior to the cells 50 entering the extensional region 50

The system 10 operates with a high throughput. Preferably, thousands of cells 50 individually flow at over 1 meter/second into the extensional region 40. After the cells 50 have been subject to the stretching forces, the cells 50 leave region B via one of microfluidic outlet channels 34, 36. As the cells 50 leave region B, another cell 50 can enter the extensional region 40 whereby it is subject to substantially the same deformation forces. This next cell 50 is imaged and leaves region B. This process is repeated many times over to enable the processing of over 1,000 cells/second in series. For example, nearly 2,000 deformations per second may be reached using the current system 10 which is more than three (3) orders of magnitude over current state-of-the-art methods for measuring the mechanical properties of cells.

Figure 12A:
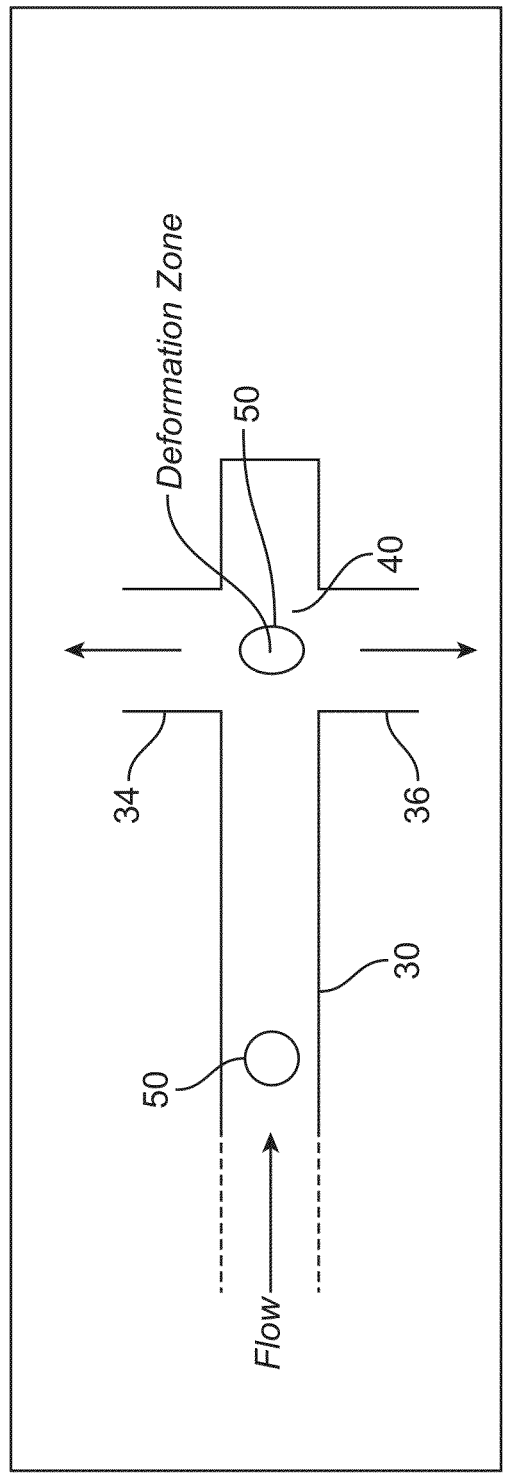
FIG. 12A illustrates a schematic view of a system for measuring cell deformability according to another embodiment.
Figure 12B:
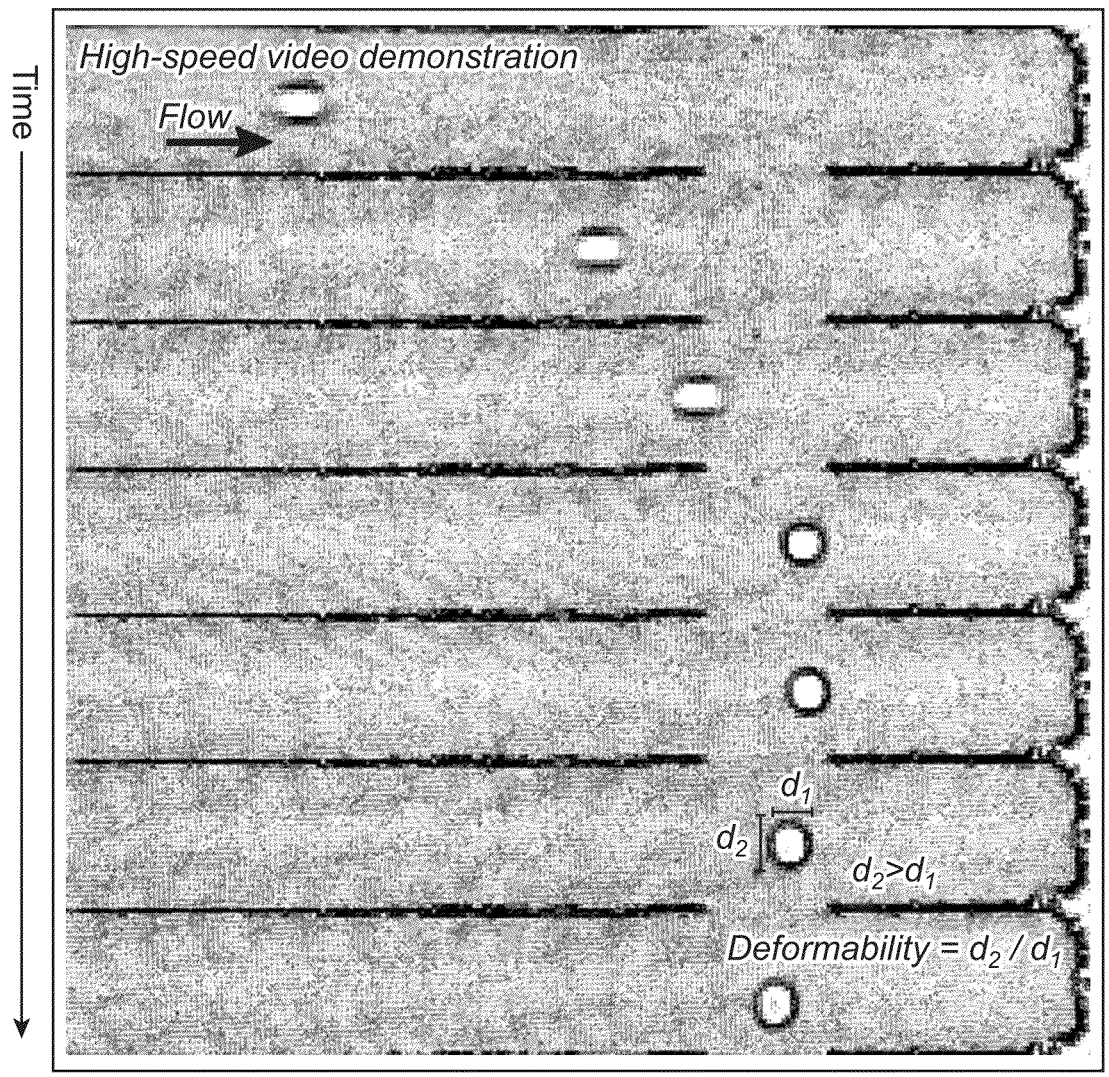
FIG. 12B illustrates photographic images of a cell passing into an extensional region at various points of time.

As an alternative to the system 10 of FIG. 1, one of the first and second microfluidic channels 30, 32 may be omitted to form a junction in the manner of a T-shape as shown in FIG. 12A. For example, the T structure may include a microfluidic channel 30 (inlet) and two outlet channels 34, 36. Thus, in this alternative embodiment fluid flows toward the junction whereupon the velocity of the flow in the incoming flow direction abruptly decreases to substantially zero. In this alternative embodiment, the other aspects of FIG. 1 remain the same (e.g., focusing, imaging, etc.). FIG. 12B illustrates a series of images taken of a cell 50 passing through a device of the type illustrated in FIG. 12A.

Referring back to FIG. 1, the system 10 includes an imaging system 60 that enables high speed images to be taken of cells 50 passing within a field of view (FOV). The FOV includes the extensional region 40 as well as some portion of the upstream segments of first and second microfluidic channels 30, 32. Similarly, the FOV may also include portions of the first and second microfluidic outlet channels 34, 36. For instance, as seen in FIG. 1, the FOV may be substantially coextensive with region B. The imaging system 60 may include a magnifying objective lens 62 that is used to magnify the view. For example, the magnifying objective 62 may include a 10× objective (Nikon Japan 10×/NA 0.30) that is affixed to a Nikon Eclipse Ti inverted microscope (not shown). The imaging system 60 further includes an imaging device 64 capable of obtaining a plurality of image frames of a FOV. The imaging device 64, in one aspect, is a digital high speed camera capable of capturing several thousand frames per second. For example, the imaging device 64 preferably operates at more than 50,000 records per second and an exposure time per record of ≤2 microseconds. While digital imagery may be obtained with a high-speed camera, other imaging modalities capable of capture rates described above may be used. For example, in some alternative embodiments, records of the FOV may be recorded by devices not having an array of pixels to capture an image frame. In this regard, data is collected by an optical collector that would replace the imaging device 64. This may include light collected onto a photodiode or photomultiplier tube (PMT). These devices may record, for example, optical contrast or scattered light which may be used to derive one or more morphological parameters.

As one example, the imaging device 64 may include a digital high-speed video camera, Phantom v7.3 (Vision Research, Inc., Wayne, N.J., USA), connected to the microscope via a c-mount for image capture. Camera settings can be controlled with Phantom Camera Control (Vision Research, Inc.). The frame rate of the camera is limited by the chosen pixel resolution. For the larger diameter (67 μm) device, 256×32 pixels was used while 128×24 pixels was used for the smaller diameter (44 μm) device. The resulting frame rates were 133,333 per second and 173,913 per second, respectively. The minimum allowable exposure time, 1 μs, was used for both devices. The device was aligned at the center of the FOV. The aperture to the imaging device 64 was half-closed to focus light and reduce scatter. Light intensity was adjusted to maximize the contrast between the cell walls and the exterior fluid.

Figure 3:
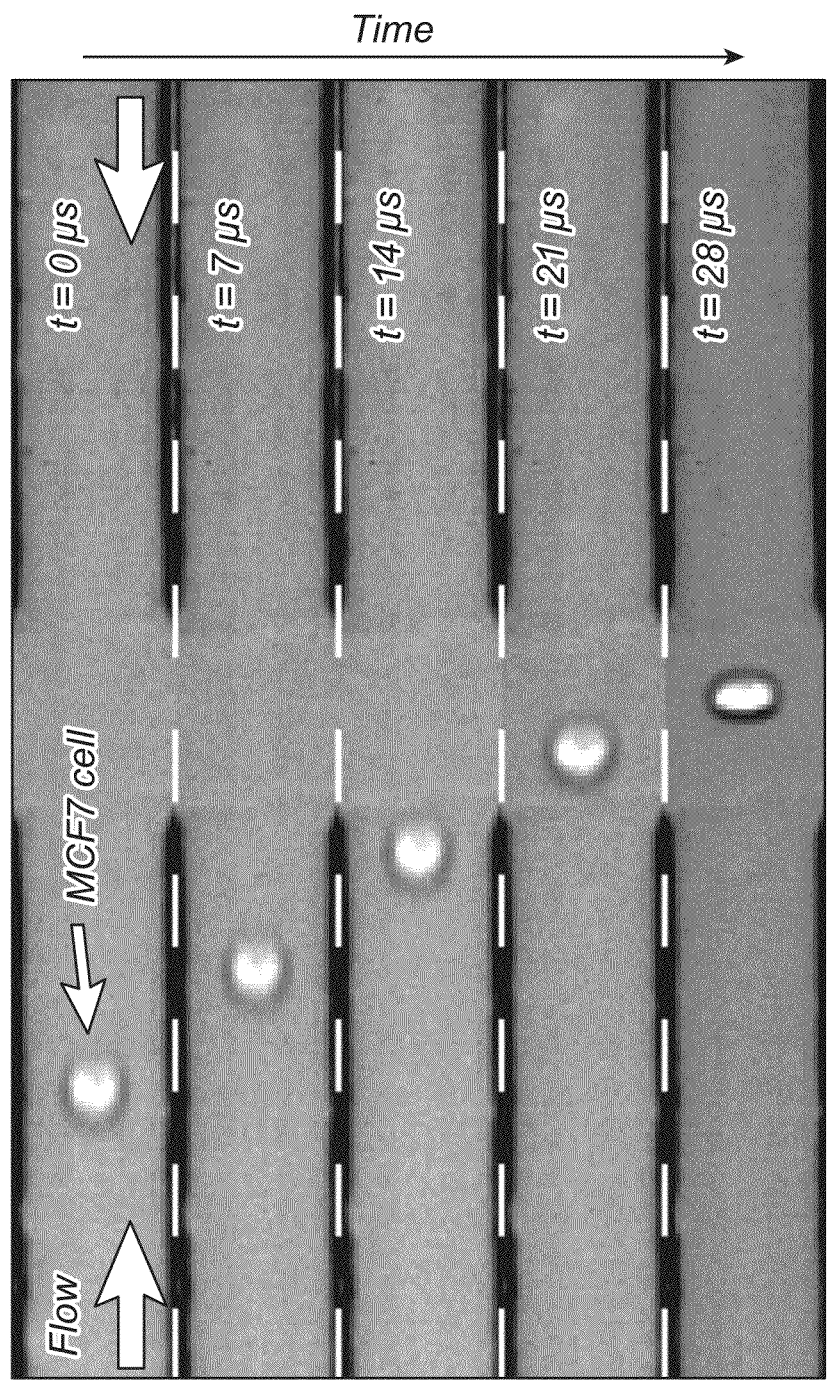
FIG. 3 illustrates photographic images of a cell passing into an extensional region at various points of time.

FIG. 3 illustrates images of a cell 50 passing into an extensional region at various time periods. The cell 50 is a MCF7 cell and is imaged at 0, 7, 14, 21, and 28 μs. Stretching of the cell 50 is clearly seen in the 28 μs image.

The system 10 further includes a computer 70 containing at least one processor therein 72. The computer 70 is used for data analysis of individual image frames obtained from the imaging device 64. The computer 70 may also be used for data acquisition purposes to store either permanently or temporarily image frames or other representative data. The computer 70 may also be used for post-processing analysis such as modeling, classification/regression tree analysis (e.g., training sets for classification trees (CART)). In still other aspects, the computer 70 may be integrated with other aspects of the system 10. For instance, the computer 70 may be used to control the flow rate of the pump 18. The computer 70 and processor(s) 72 contained therein are used to execute software contained therein for image analysis. The computer 70 also includes a display 74 that may be used to display one or more dimensional parameters of the cells 50 passing through the extensional region 40. For example, the display 74 may display to the user a cytometry-like scatter plot of data such as deformability or circularity as a function of initial cell diameter for a large batch of cells.

The software used for image analysis may reside on or otherwise be stored in the computer 70 on a computer readable medium. Alternatively, the software used for image analysis may reside in a computer readable medium at a remote location and executed with processor (not shown) that itself is remote or local. In this alternative, the remote processor is accessible via a network such as a wide area network (e.g., Internet) or local area network via the computer. In either instance, the software contains script or instructions for the automated image analysis of cells 50 passing through the system 10.

Figure 4:
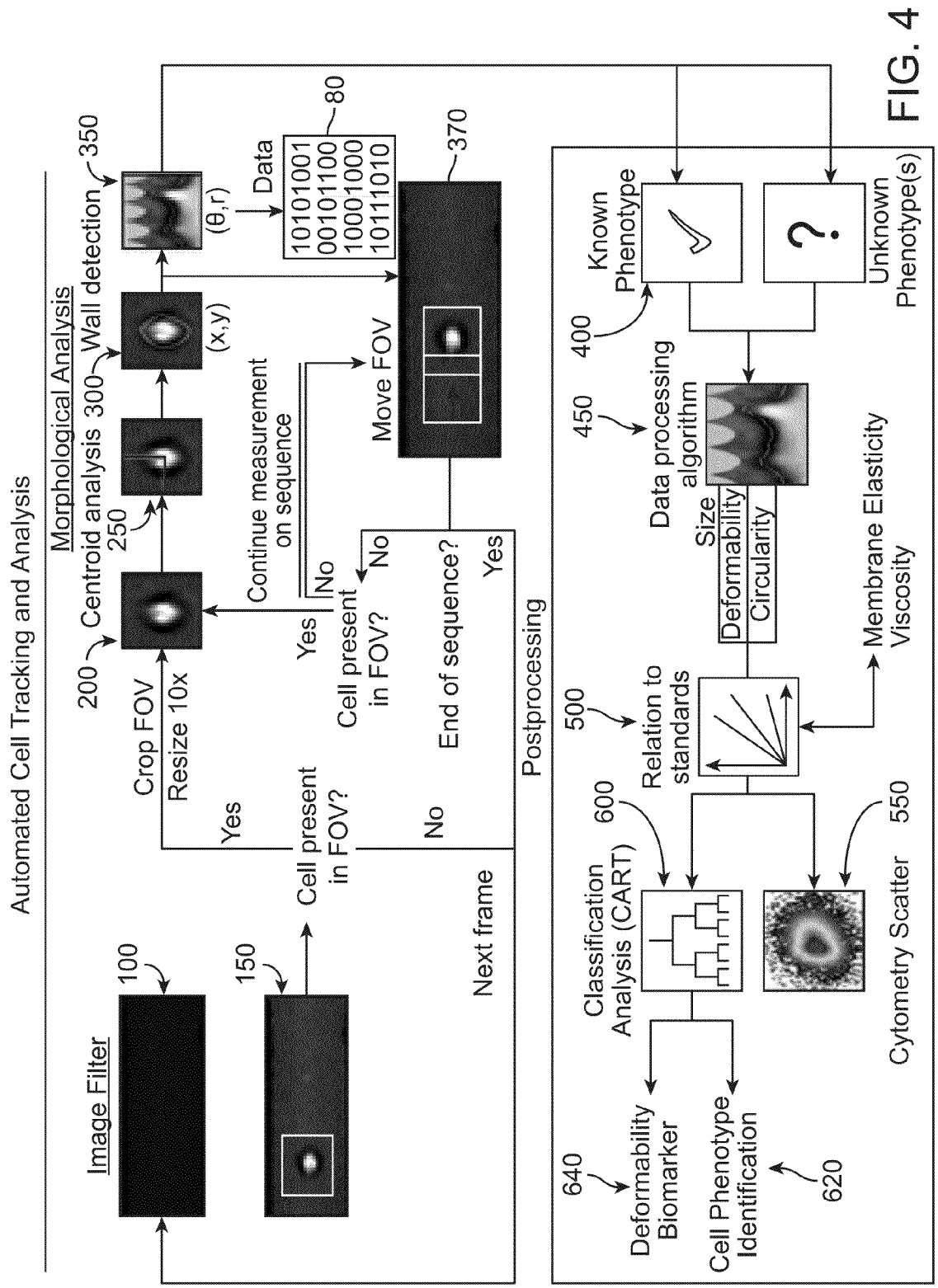
FIG. 4 illustrates an automated cell tracking analysis and post-processing algorithm according to one embodiment.

FIG. 4 illustrates an exemplary script or algorithm that is usable with the system 10. The software includes functionality for the automatic tracking and measurement of cells 50 passing through the device. The software also includes functionality for post-processing the raw data measurements made from the individual frames. The software may be implemented on any number of platforms known to those skilled in the art such as Matlab, etc. Starting at operation 100, a FOV from the imaging device 64 is subject to optional filtering to enhance cell identification by adjusting contrast, gamma, and brightness. A pre-junction channel (pre-extensional region 40) is monitored as illustrated in operation 150 for the presence or absence of a cell 50. This pre-junction channel is located in first microfluidic channel 30 upstream of the extensional region 40. If the cell 50 is not present, the next frame in the image sequence is looked at until a cell 50 is identified in the pre-junction. Once the cell 50 is identified in the FOV, as seen in operation 200, The FOV is cropped and resized 10× to increase the accuracy of measurements. Next, as seen in operation 250, a centering algorithm identifies the center of the cell 50 based on the cell position, shape, and local intensities. The image data at this point is represented in Cartesian coordinates as seen in operation 300. A polar coordinate representation of this image is then extracted (operation 350) whereby the cell as a function of (θ, r). The cell walls are found by examining changes in the intensity derivatives, and diameters extracted every several degrees. The tracking algorithm then moves the FOV as seen in operation 370 to obtain additional frames of the cell 50 until it leaves the deformation-inducing extensional region 40. Once the cell 50 has left, the process starts again at operation 100 until a next cell 50 passes into view. At this point in the process, the cell 50 has been automatically tracked through the extension region 40 and data 80 corresponding to cell diameters at intervals of several degrees (e.g., 2-3°).

Still referring to FIG. 4, post-processing (operation 450) is conducted on the data 80 to determine cell size, cell deformation, and cell circularity. The cells 50 passing through the system 10 may either be of a known phenotype or an unknown phenotype as illustrated by operation 400. As part of the post processing operation 450, the size of the cell 50 prior to entering the extensional region 40 is determined. The cell diameter (d) is determined as the average of the minimum cell diameters at 90°±30° to horizontal prior to entering the extensional region 40 (approximately four (4) frames prior to entering extension region 40). By taking the size measurements from the vertical axis, noise due to blur attributed to high velocities in the horizontal direction is reduced. As the cell 50 enters the extension region 40 and changes trajectory the deformability and circularity parameters are measured. In the frame where the largest deformation is calculated, the corresponding circularity is recorded as well. The deformability parameter is determined by the ratio a/b of the maximum diameter (a) in the vertical direction at 90°±30° to the minimum diameter (b) in the horizontal direction at 0°±30°. The circularity parameter is calculated by $(4\pi A/L^2)$ wherein A is the area of the observed cell and L is the perimeter of the cell.

Figure 5:
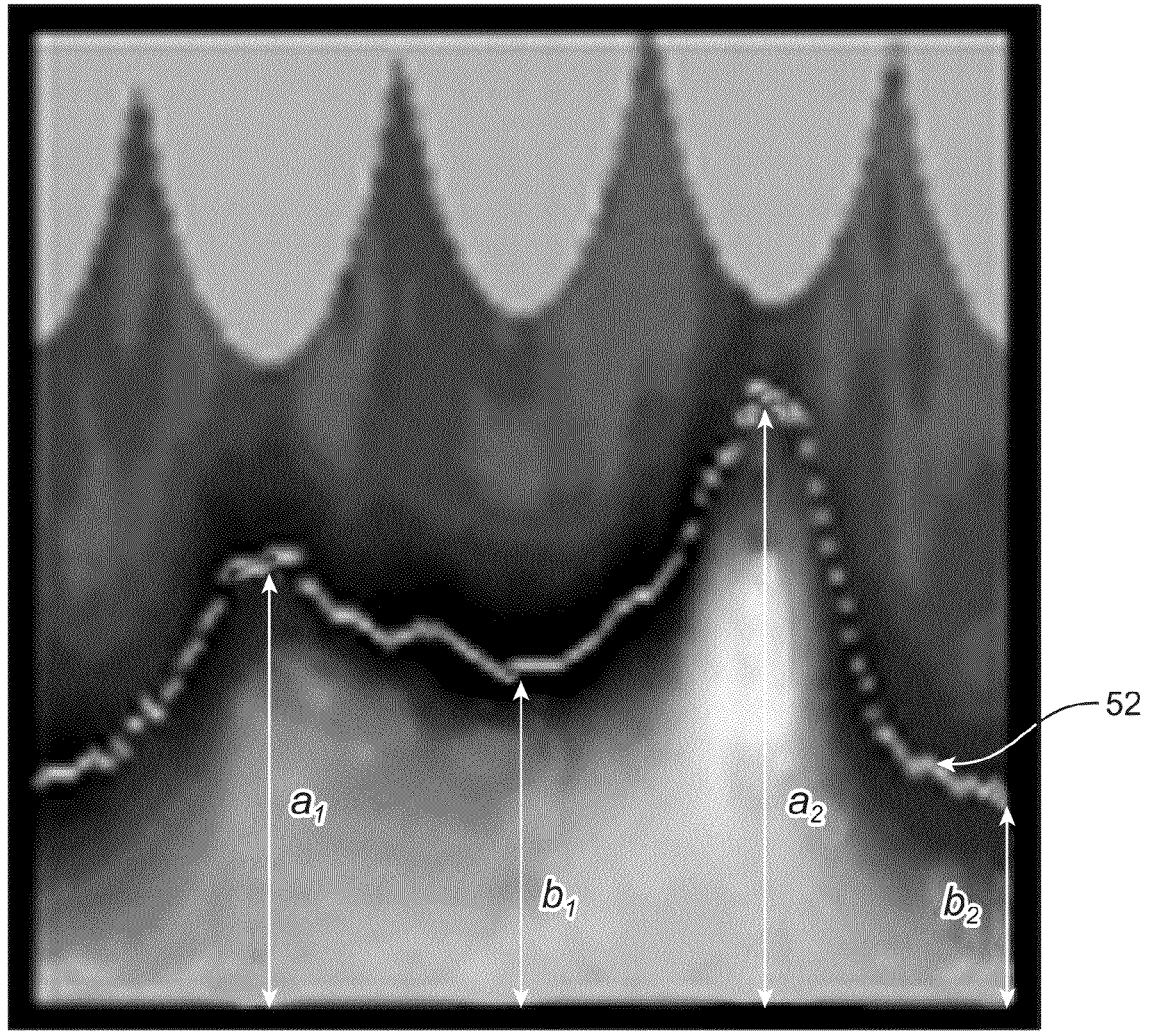
FIG. 5 illustrates a graph of the (θ, r) mapping of a single cell.

FIG. 5 illustrates a graph of the (θ, r) mapping of a single cell 50. The minimum intensity in the plot is used as the cell edge and is represented in FIG. 5 by white line 52. The maximum diameter is calculated by summing $a_1$ and $a_2$ ($a=a_1+a_2$) as illustrated in FIG. 5. The minimum diameter is calculated by summing $b_1$ and $b_2$ ($b=b_1+b_2$) as illustrated in FIG. 5. Still referring to FIG. 5, the area A of the observed cell is equal to the area under the white line 52 while the perimeter L of the cell is equal to the length of the white line 42. This information can be extracted from the data 80.

In one aspect of the invention, measurements of cells 50 whose initial diameters measure greater than a maximum threshold value are discarded as these cells 50 are bigger than the smallest channel dimension and are deforming to fit through the channels 30, 32. Measurements of cells 50 whose initial diameters measure less than a minimum threshold value are also discarded as confidence of these measurements is diminished by the small number of pixels per cell 50 at this size. For example, the maximum threshold may be set at 28 μm while the minimum threshold may be set to 5 μm. It should be understood that different threshold values than those specifically set forth above may be used. In another aspect, measurements of cells 50 are discarded when their initial diameters are greater than the third quartile plus 1.5× the interquartile range or less than the first quartile minus 1.5× the interquartile range.

Figure 6:
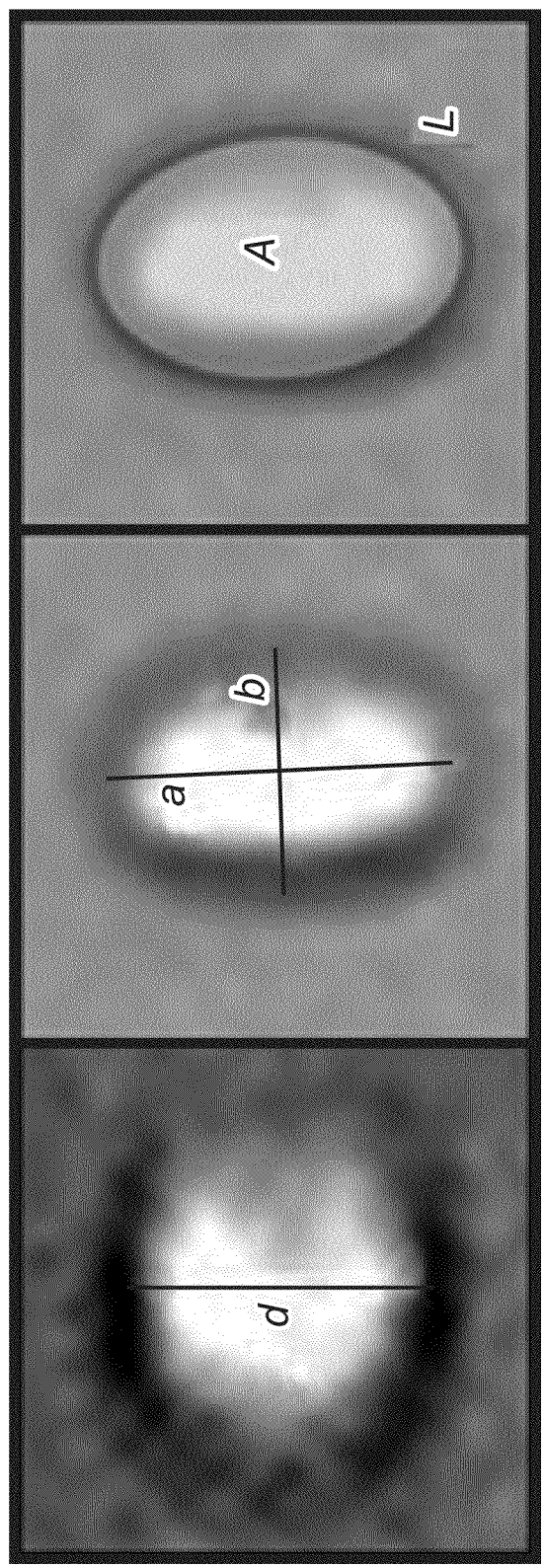
FIG. 6 illustrates images of a single cell along with dimensional indications for initial diameter (d), the maximum diameter (a) in the vertical direction, the minimum diameter (b) in the horizontal direction, the area A of the observed cell, and the perimeter L of the observed cell.

FIG. 6 illustrates micrograph images of cells 50 showing the initial diameter (d), the maximum diameter (a) in the vertical direction, the minimum diameter (b) in the horizontal direction, the area A of the observed cell, and the perimeter L of the observed cell.

Referring back to FIG. 4, after collection of the data 80, the data 80 undergoes post-processing in operation 450 to determine the initial size (d), deformability (a/b), and circularity $(4\pi A/L^2)$ of the cells 50 in the manner described above. In one optional aspect of the invention as illustrated by operation 500, modeling software contained in the computer 70 (e.g., processor(s) 72) to obtain additional information on the cells 50 like membrane elasticity or viscosity. For example, the time dynamics of deformation and relaxation of the cell 50 after stress is removed can provide viscoelastic properties of the cells. A time constant for deformation may be extracted from a plot of the deformed shape of the cell 50 as a function of time. The same can be done for relaxation of the cell 50 after removal of the stress.

In another alternative embodiment, operation 500 is omitted and two-dimensional (2D) scatter plots are generated of one or more of the parameters (e.g., size, deformability, circularity) as illustrated in operation 550. The scatter plots may include, for example, initial size as a function of deformability or initial size as a function of circularity. The scatter plots may be displayed to the user on a display 74 that is connected to the computer 70. The scatter plots contain large datasets that allow the presentation of statistically rich deformability data to the user, allowing definitive conclusions concerning cell mechanical properties. Moreover, users will be able to easily use this information in part because of their familiarity to existing scatter plots for flow cytometry.

Instead of being displayed to the user in scatter plot format, the datasets may be then tested in classification and regression tree analysis as is illustrated in operation 600. This can be used to either determine cell phenotype 620 or it may be used to provide a deformability biomarker 640 that can then be used for identification and routine screening for clinical use.

Experiment No. 1—Differentiation of Embryonic Stem Cells

Figure 7A:
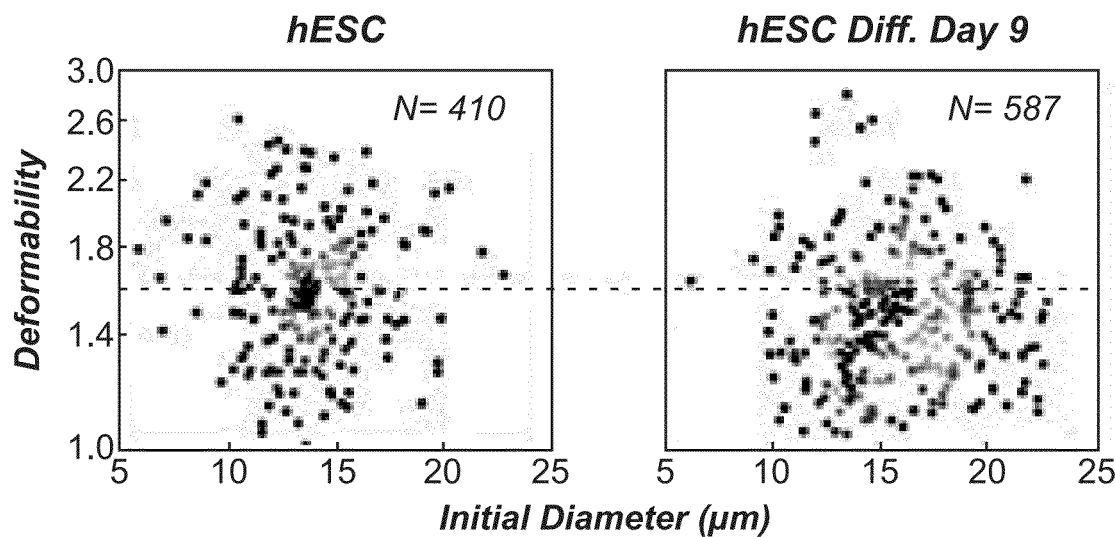
FIG. 7A illustrates scatter plots of cell deformability as function of initial diameter for human embryonic stem cells (hESCs) and hESCs undergoing differentiation (day 9).
Figure 7B:
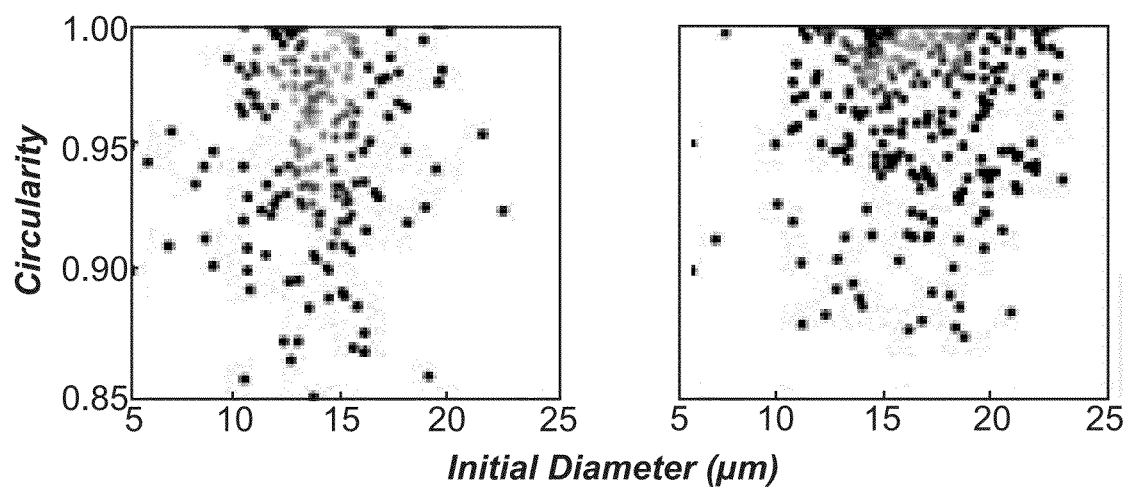
FIG. 7B illustrates scatter plots of cell circularity as function of initial diameter for human embryonic stem cells (hESCs) and hESCs undergoing differentiation (day 9).

Experiments were conducted using the system to determine the ability to using deformability as biomarker of the "sternness" of embryonic stem cells. Embryonic stem cells are known to have more deformable nuclei and are known to be more deformable than differentiated cells. In this experiment, the HSF-1 line of human embryonic stem cells (hESCs) (46XY Karyotype) were tested in the system at flow rates between 700-800 μL/min. FIGS. 7A and 7B illustrates the unique deformability and circularity signatures, respectively, for human embryonic stem cells (hESCs) and hESCs undergoing differentiation (day 9). N refers to the number of cells represented in the particular scatter plot. Medians for the two populations are different with statistical significance P<0.001. Unique differences in circularity are also evident (FIG. 7B).

Experiment No. 2—Differentiation of Embryonic Stem Cells

Experiments were also conducted using the system to determine the deformability of self-renewing mouse embryonic stem cells (mESC) differentiated by adherent (Ad. Diff.) and embryoid body (EB Diff.) methods. Undifferentiated mESC lines were cultured in 5.0% $CO_2$ at 37° C. on mitomycin C-inactivated CF1 mouse embryonic fibroblast cells. Culture medium contained KnockOut Dulbecco's modified Eagle's medium (DMEM), 15% fetal calf serum, 1× non-essential amino acids (Invitrogen/GIBCO, 100× concentration), 1× Pen Strep Glutamine (Invitrogen/GIBCO, 100× concentration), 0.055 mM 2- mercaptoethanol (Invitrogen/GIBCO, 1000× concentration, 55 mM), and 55 units leukemia inhibitory factor (Millipore, 106 units/ml). Mouse ESCs were differentiated into either embryoid bodies (EBs) as hanging drops or adherent culture on gelatin. Differentiation medium contained KnockOut (DMEM), 15% fetal calf serum, 1× nonessential amino acids, 1× Pen Strep Glutamine, and 0.055 mM 2-mercaptoethanol. EBs were collected at day 9 for analysis. For adherent culture, 15,000 cells were plated on gelatin-coated six-well plates in mESC differentiation medium. Media was changed at day 4, 5 and 6. At day 9, cells were collected for analysis.

Figure 8A:
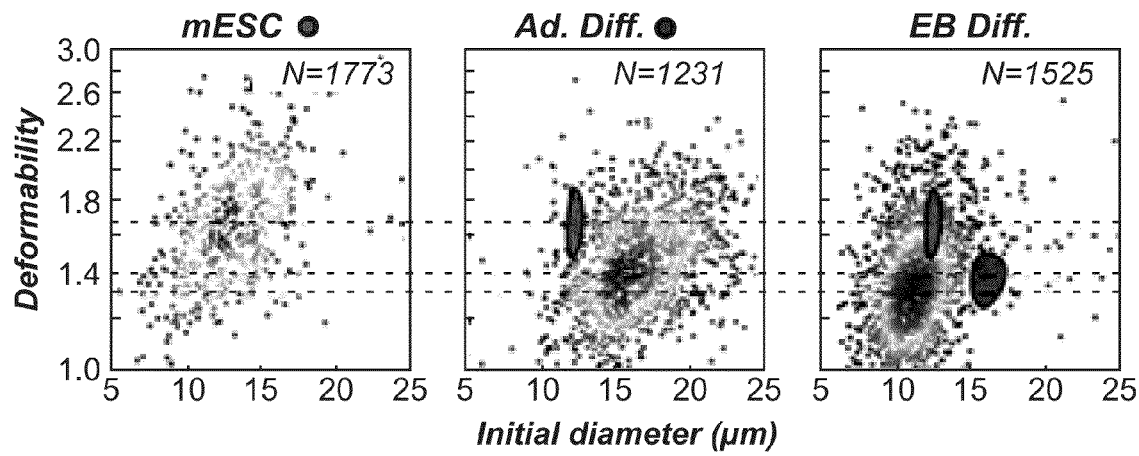
FIG. 8A illustrates scatter plots of cell deformability as function of initial diameter for undifferentiated mESC, differentiated stem cells with Ad. Diff., and differentiated stem cells with EB Diff.
Figure 8B:
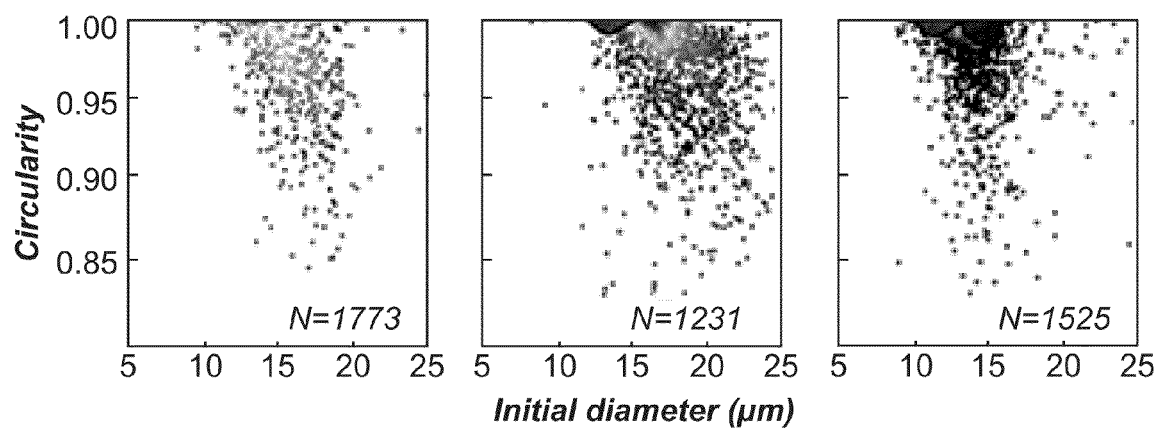
FIG. 8B illustrates scatter plots of cell circularity as function of initial diameter for undifferentiated mESC, differentiated stem cells with adherent differentiation, and differentiated stem cells with embryoid body differentiation.

FIG. 8A illustrates deformability measurements made using the system for undifferentiated mESC, differentiated stem cells with Ad. Diff., and differentiated stem cells with EB Diff. FIG. 8B illustrates circularity measurements made using the system for undifferentiated mESC, differentiated stem cells with Ad. Diff., and differentiated stem cells with EB Diff. N refers to the number of cells represented in the particular scatter plot. Both differentiation methods (Ad. Diff. and EB Diff.) result in an increase in cell stiffness. This statistically significant difference validates findings that differentiation state and associated cytoskeletal changes may manifest as a difference in cell mechanics. This distinction may find application in identifying failed-to-differentiate stem cells destined for implantation which could otherwise result in tumors in vivo.

Experiment No. 3—Measurement of Metastatic Potential of Cancer Cells

Experiments were also conducted to measure and classify breast cancer cells by metastatic potential. FIGS. 9A and 9B illustrate measurements of deformability and circularity, respectively, for normal cells (MCF10A), cancerous cells (MCF7), and the same cancerous cell line modified to have increased motility or metastatic potential (modMCF7). N refers to the number of cells represented in the particular scatter plot. The MCF10A cell line (ATCC Number: CRL-10317) was cultured in DMEM-F12 with horse serum at a final concentration of 5% (v/v), penicillin/streptomycin 1% (v/v), 20 nM epidermal growth factor, 0.5 µM hydrocortizone, 0.1 µM cholera toxin, and 10 µM insulin. The MCF7 cell line (ATCC Number: HTB-22) was propagated in DMEM-F12 with 0.01 mg/mL bovine insulin and fetal bovine serum at a final concentration of 10% (v/v). Modification to make the cell line more invasive, designated "modMCF7" was carried out by incubation with 400 nM 12-Otetradecanoylphorbol-13-acetate (TPA) for 20 hours.

Measurements of both deformability and circularity clearly distinguish normal cells from cancerous cells and malignant cells. The medians were determined by a nonparametric test to be statistically different with a confidence of P<0.01. This confirms trends observed by other techniques for measuring cell mechanical properties with greatly enhanced throughput, enabling adoption of the technique in settings where analysis of diverse cell populations is necessary.

Experiment No. 4—Cytoskeletal Disruption

Experiments were conducted measuring cell deformability of cervical carcinoma cells (HeLa) treated with the actin disruptor Latrunculin. HeLa cells were also treated with Nocodazole, a microtubule stabilizer, and measured for cell deformability. The HeLa cell line was maintained in with DMEM-F12 with 1% (v/v) penicillin/streptomycin and 10% (v/v) fetal bovine serum. To explore the effects of cytoskeleton components on deformability, microtubules were inhibited with Nocodazole and disrupted actin polymerization with Latrunculin A. Cells were incubated in 0.1 µM Latrunculin A for 4 hours and/or 2 µM nocodazole for 1 hour, respectively, prior to deformability assay.

FIGS. 10A and 10B illustrate deformability and circularity measurements, respectively, made with the system 10 for HeLa cells (control), HeLa cells treated with Latrunculin A, and HeLa cells treated with Nocodazole. N refers to the number of cells represented in the particular scatter plot. HeLa cells treated with Latrunculin were measured to be significantly more deformable. HeLa cells treated with Nocodazole appear more rigid than untreated cells.

Figure 11A:
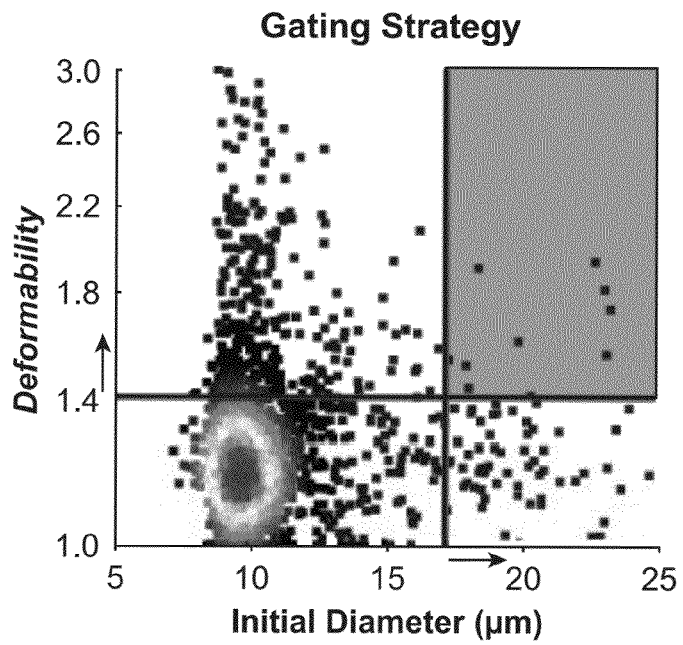
FIG. 11A illustrates one embodiment of a gating strategy that looks for cell percentage that exists in a region of high initial diameter and high deformability (darkened region in upper right quadrant).
Figure 11B:
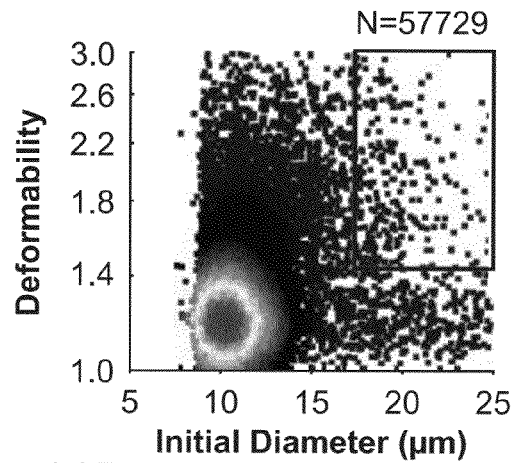
FIG. 11B illustrates a scatter plot of cell deformability as function of initial diameter for a standard negative profile (non-cancerous).
Figure 11C:
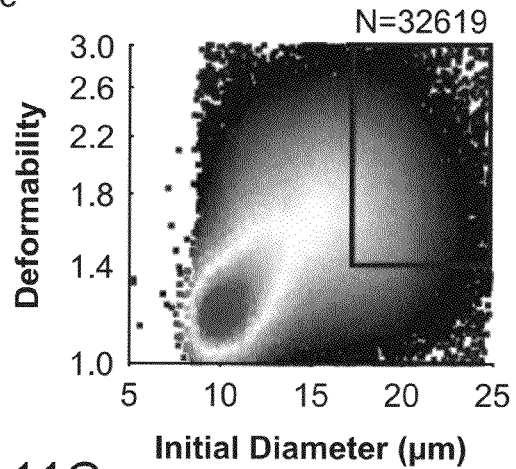
FIG. 11C illustrates a scatter plot of cell deformability as function of initial diameter for a standard adenocarcinoma profile.

Turning now to a particular use of the system 10, the same may be used to diagnose a disease state. For example, a gating strategy may be employed wherein large, highly deformable (LDH) cells are used as a proxy for targeting metastatic cancer. For example, the system 10 may be used to test pleural fluid obtained from a subject. The sample may be run through the system 10 to diagnose carcinomas or other malignancies. A threshold may be established requiring a certain percentage of cells be LDH; namely the cells have an initial diameter above a certain threshold value and a deformability above a certain threshold value. FIG. 11A illustrates such a gating strategy whereby the darkened region with high deformation and high initial diameter is queried to determine the overall percentage of cells falling in this region. N refers to the number of cells represented in the particular scatter plot. FIG. 11B illustrates a standard negative profile whereby the LHD % is low (in this case 0.9%). This contrasts with the standard adenocarcinoma profile illustrated in FIG. 11C whereby the LHD % is high (in this case 21.3%). The scatter plots of deformability may also be used in the same way to make negative determinations. The data can further be used to determine those instances wherein additional review is needed by a cytologist or additional testing is needed, atypical cells are present, and inflammation conditions exist. Additional gating schemes other than standard thresholding may also be used. For instance, gating functions established via models or prior experimental datasets can be used to identify a subset of cells based on pre-established criteria based at least in part on cell size and deformability.

The system 12 may also be used for identifying biomarkers that correspond to various cellular properties. These include, by way of example, malignancy, metastatic potential, cell cycle stage, differentiation stage, cytoskeletal integrity, and leukocyte activation.

Advantages of the system 10 over other existing analysis techniques include reduced reagent consumption. Moreover there is less need for labor given that there is no need for pipetting, centrifugation, etc. The system 10 also allows operation on smaller volumes without cell loss which might arise in processing steps such as centrifugation and cell handling. The system 10 further has a very high throughput that is multiple orders of magnitude higher than existing techniques for measuring cell deformability.

While embodiments have been shown and described, various modifications may be made without departing from the scope of the inventive concepts disclosed herein. For example, while several embodiments have been described herein it should be appreciated that various aspects or elements are interchangeable with other separately embodiments. The invention(s), therefore, should not be limited, except to the following claims, and their equivalents.

What is claimed is:

1. A system for measuring a morphological parameter of a cell comprising:
   a substrate containing first and second microfluidic channels dimensioned to carry cells therein;

an extensional region comprising an intersection of the first and second microfluidic channels, wherein the first and second microfluidic channels intersect in substantially opposite directions;
a pump configured to flow a plurality of cells into at least one of the first and second microfluidic channels;
a focusing region located in at least one of the first and second microfluidic channels upstream of the extensional region, wherein the focusing region focuses cells passing there through into a stream of cells located along one or more lateral streamlines;
at least one outlet channel coupled to the extensional region;
an imaging device configured to capture a plurality of image frames of the cells passing through the extensional region at a rate of at least 1,000 cells/second; and
at least one processor configured to calculate a morphological parameter of each cell passing through the extensional region, wherein the cells are flowed through the extensional region and the morphological parameter comprises a measured dimension or dimensional change of the cell passing through the extensional region.

2. The system of claim 1, wherein the morphological parameter is selected from the group of cell size, cell deformability, and cell circularity of cells passing through the extensional region.

3. The system of claim 2, wherein the morphological parameter further comprises at least one of cell shape, cell granularity, and intracellular structure.

4. The system of claim 1, wherein the first and second microfluidic channels are substantially coaxially aligned with respect to one another.

5. The system of claim 1, wherein the at least one outlet channel comprises first and second outlet channels arranged substantially perpendicular to the first and second microfluidic channels.

6. The system of claim 1, wherein the first and second microfluidic channels are coupled to a common inlet at an upstream location and the pump is coupled to the common inlet.

7. The system of claim 6, wherein the cells pumped into the common inlet have a density within the range between about 200,000 cells/mL and about 500,000 cells/mL.

8. The system of claim 1, further comprising a display configured to display at least one of cell deformability and cell circularity calculated by the at least one processor.

9. The system of claim 8, wherein the at least one processor is configured to identify a subset of cells having a calculated cell deformability or calculated cell circularity above a threshold level.

10. The system of claim 8, wherein the at least one processor is configured to calculate cell size and cell deformability of cells passing through the extensional region and the at least one processor is configured to identify a subset of cells having a threshold cell size and deformability.

11. The system of claim 1, wherein the at least one processor is part of a computer.

12. The system of claim 11, further comprising a computer readable medium containing program instructions for the at least one processor for calculating one or more of cell size, cell deformability, and cell circularity of cells passing through the extensional region.

13. A method of measuring cell deformability comprising:
focusing a plurality of cells in first and second microfluidic channels dimensioned to carry cells therein;
intersecting the cells of the first and second microfluidic channels in an extensional region configured to apply stress to cells passing into the extensional region with a velocity of at least 1 meter/second;
obtaining a plurality of image frames of the cells, wherein the plurality of image frames contain images of cells prior to entering the extensional region, during, and following exposure to the stress applied in the extensional region;
measuring one or more dimensional parameters of the cells from the plurality of image frames prior to entering the extensional region and during and after exposure to the stress applied in the extensional region; and
calculating the deformability of a cell using the at least one processor configured to calculate one or more dimensional parameters occurring during exposure to the stress applied in the extensional region.

14. The method of claim 13, wherein the one or more dimensional parameters comprises measuring the diameter of individual cells prior to entering the extensional region.

15. The method of claim 13, wherein the one or more dimensional parameters comprises measuring maximum and minimum diameters of individual cells during exposure to the extensional region.

16. The method of claim 13, wherein determining deformability comprises calculating a ratio of the maximum cell diameter to the minimum cell diameter.

17. The method of claim 13, further comprising calculating the circularity of a cell wherein circularity is calculated according to the formula $4\pi A/L^2$, wherein A comprises cell area and L comprises cell perimeter.

18. The method of claim 13, wherein the first and second microfluidic channels intersect in substantially opposite directions.

19. The method of claim 13, further comprising displaying on a display at least one of deformability and circularity as a function of cell diameter calculated by the at least one processor.

20. The method of claim 13, further comprising calculating at least one of membrane elasticity and viscosity.

21. The method of claim 13, further comprising measuring one or more morphological parameters of the cells prior to the cells entering the extensional region.

22. A system for measuring a morphological parameter of a cell comprising:
a substrate containing a microfluidic channel dimensioned to carry cells therein;
an extensional region comprising a junction wherein the velocity of the flow abruptly changes to an orthogonal flow direction from the incoming flow direction;
a pump configured to flow a plurality of cells into the microfluidic channel;
a focusing region located in the microfluidic channel upstream of the extensional region, wherein the focusing region focuses cells passing there through into a stream of single cells located along one or more lateral streamlines;
at least one outlet channel coupled to the junction of the extensional region;
an imaging device configured to capture a plurality of image frames of cells passing through the extensional region at a rate of at least 1,000 cells/second; and
at least one processor configured to calculate a morphological parameter of each cell passing through the extensional region, wherein the morphological parameter comprises a measured dimension or dimensional change of the cell passing through the extensional region.

23. A system for measuring a morphological parameter of a cell comprising:

a substrate containing first and second microfluidic channels dimensioned to carry cells therein;

an extensional region comprising an intersection of the first and second microfluidic channels, wherein the first and second microfluidic channels intersect in substantially opposite directions;

a pump configured to flow a plurality of cells into at least one of the first and second microfluidic channels;

a focusing region located in at least one of the first and second microfluidic channels upstream of the extensional region, wherein the focusing region focuses cells passing there through;

at least one outlet channel coupled to the extensional region;

an imaging device configured to capture a plurality of image frames of the cells passing through the extensional region, wherein each cell passes through the extensional region in less than 500 µs; and at least one processor configured to calculate a morphological parameter of each cell passing through the extensional region, wherein the cells are flowed through the extensional region and the morphological parameter comprises a measured dimension or dimensional change of the cell passing through the extensional region.

* * * * *